United States Patent [19]

Wampler

[11] 4,349,539

[45] Sep. 14, 1982

[54] SEPARATION OF HEPATITIS B SURFACE ANTIGEN

[75] Inventor: D. Eugene Wampler, Harleysville, Pa.

[73] Assignee: Merck & Co., Inc., Rahway, N.J.

[21] Appl. No.: 178,340

[22] Filed: Aug. 15, 1980

[51] Int. Cl.³ ..................... A61K 39/12; A61K 39/29
[52] U.S. Cl. ........................................ 424/89; 424/86; 424/88; 260/112 B
[58] Field of Search ................. 424/88, 89, 86, 112 R, 424/101; 260/112 B

[56] References Cited

U.S. PATENT DOCUMENTS

| | | | |
|---|---|---|---|
| 4,024,243 | 5/1977 | McAleer et al. | 424/89 |
| 4,088,748 | 5/1978 | McAleer et al. | 424/89 |
| 4,181,713 | 1/1980 | McAleer et al. | 260/112 R |
| 4,204,989 | 5/1980 | McAleer et al. | 424/88 |

FOREIGN PATENT DOCUMENTS 2150559  4/1973  France .

OTHER PUBLICATIONS

Schmitthauesier, R., Process Biochemistry, pp. 13-15, 46, 1977.

*Primary Examiner*—Blondel Hazel
*Attorney, Agent, or Firm*—Donald J. Perrella; Hesna J. Pfeiffer

[57] ABSTRACT

Fluid containing hepatitis B surface antigen (HBsAg) is concentrated and separated from contaminating material by ultrafiltration before undergoing further processing to isolate HBsAg.

7 Claims, No Drawings

SEPARATION OF HEPATITIS B SURFACE ANTIGEN

BACKGROUND OF THE INVENTION

The isolation of hepatitis B surface antigen (HBsAg) from positive plasma or serum by ultracentrifugation, column chromatography, etc., is known. When ultracentrifugation is used, the small size of the HBsAg particle (about 20 nm) requires about 18 hours per batch for the centrifugation step. Due to this time requirement, centrifugation becomes the limiting step in producing HBsAg.

OBJECTS OF THE INVENTION

It is an object of the present invention to provide an improved method for preparing HBsAg. Another object is to provide a method whereby centrifugation time can be reduced significantly. These and other objects of the present invention will be apparent from the following description.

SUMMARY OF THE INVENTION

Fluid containing HBsAg is concentrated by ultrafiltration to reduce its volume while retaining substantially all of the HBsAg and removing many contaminants. Because of the increased concentration more antigen can be processed to a final product in the same time.

DETAILED DESCRIPTION

The present invention relates to the separation of HBsAg from HBsAg-containing fluid and, more particularly, to a method of concentrating the fluid before further purification.

It has now been found that the volume of HBsAg-containing fluids such as, for example, plasma or serum, can be greatly reduced and concentrated by ultrafiltration so that more antigen can be processed in the same centrifugation time.

The HBsAg-containing fluid may be, for example, plasma, serum, cell culture fluids, or an HBsAg-containing fraction of one or more foregoing fluids, for example, an ethanol or ammonium sulfate precipitate of plasma.

The HBsAg may be separated from the HBsAg containing fluid or derivative thereof by ultracentrifugation. The ultracentrifugation may be carried out by an isopycnic banding followed by a rate zonal banding. As each banding step requires about 18 hours, the total centrifugation time to isolate HBsAg from a single lot of plasma or serum is about 36 hours. This long time combined with the very high cost of the ultracentrifuge machines themselves makes the centrifugation step very expensive and the limiting step in the separation of HBsAg.

The separation of HBsAg by isopycnic banding and rate zonal banding is described in more detail in U.S. Pat. Nos. 4,024,243, and 4,088,748, which are hereby incorporated by reference.

By concentrating the fluid before further purification according to the present invention, up to about 25 times as much HBsAg-containing fluid can be processed without increasing the centrifugation time. A typical centrifuge, Electronucleonics K, can process about 1.7 liters at a time. With the use of the present invention, however, this same centrifuge can process in the same time material having an initial volume (before concentration) of about 40 liters.

As ultrafiltration can reduce the volume of HBsAg-containing fluid to about 1/25 or less of its original volume, 25 or more lots can be processed in the time ordinarily required to process a single unconcentrated lot. This is a significant improvement as it increases the capacity of each centrifuge about 25 fold. As ultracentrifuges are very expensive pieces of equipment and as centrifugation time is the bottleneck or limiting step in HBsAg production, the present invention significantly increases production with no increase in investment in ultracentrifuges. While the degree of concentration may be varied, generally the fluid is concentrated to not more than about 1/5 its initial volume and preferably to about 1/25 its initial volume.

By employing a filter which passes material having a size smaller than that of the HBsAg, the antigen is purified as well as concentrated. Preferably, the filter has a pore size which passes material below about 1,000,000 daltons.

The following example illustrates the present invention without, however, limiting the same thereto:

EXAMPLE 1

HBsAg positive plasma (40 liters) having a total protein content of 2760 g, and total HBsAg content of $11.3 \times 10^6$ complement fixation (CF) units is converted to serum (42 liters). An equal volume of ammonium sulfate solution (450 g/liter) is added to the filtrate which is then agitated gently overnight at 5° C. The precipitate which forms is collected by batch centrifugation at $7,000 \times$ g for 30 minutes using the JA-10 rotor (3 liter capacity per batch). The pellets post centifugation are suspended in about 4.5 liters of phosphate buffered saline (PBS), diluted to a volume of 21 liters in PBS and clarified by passing through a filter (Millipore AP 25293).

The clarified solution is concentrated to a volume of $1.2 \pm 0.4$ liters using a 4.6 square meter ultrafiltration cassette (Millipore PSVP). The concentrate is diafiltered with $4 \times 1.5$ liters of PBS. After recovering the diafiltered concentrate, the cassette is rinsed with $3 \times 250$ ml of PBS and the rinse liquid is added sequentially to the concentrate to give a final volume of $1.7 \pm 0.05$ liters having a protein content of 306 g.

The final volume is reduced about 25 fold with respect to the initial serum volume (42 liters to 1.7 liters) and the protein content is reduced 89% (2760 g to 306 g). With respect to the ammonium sulfate product, the volume and protein reductions are 12 fold and 47% (21 liters to 1.7 liters and 717 g to 306 g) while about 94% of the initial HBsAg is retained ($7.16 \times 10^6$ CF units to $6.75 \times 10^6$ CF units).

The HBsAg concentrate which is produced can be further purified, for example, by ultracentrifugation as described in the aforementioned U.S. patents. The effective ultracentrifugation capacity is increased about 25-fold.

What is claimed is:

1. In a method of separating HBsAg from a fluid containing HBsAg, the improvement which comprises centrifuging the fluid to collect a precipitate containing HBsAg, forming a suspension of the precipitate and concentrating the fluid by ultrafiltration to a volume not more than about 1/5 the initial volume.

2. A method according to claim 1 wherein the fluid is concentrated to about 1/25 its initial volume.

3. A method according to claim 1 wherein the fluid is plasma, serum or cell culture fluid, or a derivative thereof.

4. A method according to claim 3 wherein the derivative is a protein precipitate of serum.

5. A method according to claim 4 wherein the precipitate is obtained by treating the serum with ammonium sulfate.

6. A method according to claim 1 wherein the filter has a pore size that retains material above about 1,000,000 daltons.

7. A method for removing contaminants from a fluid containing HBsAg which comprises ultrafiltering the fluid using a filter which passes materials below about 1,000,000 daltons.

* * * * *